US012582471B1

(12) United States Patent
Moore et al.

(10) Patent No.: US 12,582,471 B1
(45) Date of Patent: Mar. 24, 2026

(54) GOLD PARTICLES AND USES THEREOF

(71) Applicant: ELUX MEDICAL, INC., Wilmington, DE (US)

(72) Inventors: Robert Kelly Moore, Coronado, CA (US); Jordan Sebastian Warburg, La Jolla, CA (US)

(73) Assignee: ELUX MEDICAL, INC., Wilmington, DE (US)

( * ) Notice: Subject to any disclaimer, the term of this patent is extended or adjusted under 35 U.S.C. 154(b) by 0 days.

(21) Appl. No.: 19/069,020

(22) Filed: Mar. 3, 2025

Related U.S. Application Data

(60) Provisional application No. 63/698,277, filed on Sep. 24, 2024.

(51) Int. Cl.
*A61B 18/20* (2006.01)
*A61B 18/00* (2006.01)

(52) U.S. Cl.
CPC .. *A61B 18/203* (2013.01); *A61B 2018/00464* (2013.01); *A61B 2018/00577* (2013.01)

(58) Field of Classification Search
CPC ........ A61B 18/203; A61B 2018/00464; A61B 2018/00577
USPC ............................................................ 606/2
See application file for complete search history.

(56) References Cited

U.S. PATENT DOCUMENTS

| | | | |
|---|---|---|---|
| 6,344,272 B1 | 2/2002 | Oldenburg et al. | |
| 6,530,944 B2 | 3/2003 | West et al. | |
| 6,605,080 B1 | 8/2003 | Altshuler et al. | |
| 6,685,986 B2 | 2/2004 | Oldenburg et al. | |
| 7,060,061 B2 | 6/2006 | Altshuler et al. | |
| 7,371,457 B2 | 5/2008 | Oldenburg et al. | |
| 8,430,919 B2 | 4/2013 | Bornstein | |
| 8,802,154 B2 * | 8/2014 | Harris | A61P 29/00 424/401 |
| 9,675,953 B2 | 6/2017 | Oldenburg et al. | |

(Continued)

FOREIGN PATENT DOCUMENTS

| | | |
|---|---|---|
| WO | 2012027728 A2 | 3/2012 |
| WO | 2013169955 A1 | 11/2013 |

(Continued)

OTHER PUBLICATIONS

Anderson and Parrish, Selective Photothermolysis: Precise Microsurgery by Selective Absorption of Pulsed Radiation. Science. Apr. 29, 1983;220(4596):524-527.

(Continued)

*Primary Examiner* — Aaron F Roane
(74) *Attorney, Agent, or Firm* — Michael A. Whittaker

(57) ABSTRACT

The present disclosure in various aspects and embodiments provides, inter alia, systems and methods for minimally-invasive lipolysis in a target area by injecting the area with a solution of photo-absorbing nanoparticles and irradiating the injected area with a beam of near infrared (NIR) light. The NIR emission wavelength may in certain embodiments be adapted to excite the nanoparticles to melt fat within the target area; in some embodiments so that the liquefied fat can be aspirated from the target area, or in some embodiments such that aspiration of the liquified fat is not needed. In certain aspects and embodiments the nanoparticles are be gold nanoshells; for example, spherical gold nanoshells.

17 Claims, 3 Drawing Sheets demonstration of the injection angle into the porcine tissue and device being injected as the needle is removed.

(56) References Cited

U.S. PATENT DOCUMENTS

| | | | |
|---|---|---|---|
| 10,271,904 | B2 | 4/2019 | Islam |
| 11,628,010 | B2 | 4/2023 | Almutairi et al. |
| 11,826,087 | B2 | 11/2023 | Harris et al. |
| 2008/0241262 | A1* | 10/2008 | Lee ........................... B22F 1/17 |
| | | | 428/407 |
| 2012/0059307 | A1* | 3/2012 | Harris ....................... A61P 1/04 |
| | | | 977/773 |
| 2016/0236005 | A1* | 8/2016 | Almutairi ................ A61K 8/19 |
| 2024/0189029 | A1* | 6/2024 | Schwartz ............. A61N 5/0601 |

FOREIGN PATENT DOCUMENTS

| | | | |
|---|---|---|---|
| WO | 2015054493 | A1 | 4/2015 |
| WO | 2018112261 | A1 | 6/2018 |

OTHER PUBLICATIONS

Arai et al., Biomedical Applications and Safety Issues of Gold Nanoparticles. Toxicol Environ Health Sci. 2012;4(1):1-8.

Arnida et al., Geometry and Surface Characteristics of Gold Nanoparticles Influence their Biodistribution and Uptake by Macrophages. Eur J Pharm Biopharm. Apr. 2011;77(3):417-423.

Bartneck et al., Rapid Uptake of Gold Nanorods by Primary Human Blood Phagocytes and Immunomodulatory Effects of Surface Chemistry. ACS Nano. Jun. 22, 2010;4(6):3073-3086.

Bowman and Balasubramaniam, A New Technique Utilizing Thermistor Probes for the Measurement of Thermal Properties of Biomaterials. Cryobiology. Oct. 1976;13(5):572-580.

Chen et al., Assessment of the In Vivo Toxicity of Gold Nanoparticles. Nanoscale Res Lett. May 8, 2009;4(8):858-864.

Favi et al., Shape and surface chemistry effects on the cytotoxicity and cellular uptake of metallic nanorods and nanospheres. J Biomed Mater Res A. Dec. 2015;103(12):3940-3955.

Fent et al., Biodistribution of maltose and gum arabic hybrid gold nanoparticles after intravenous injection in juvenile swine. Nanomedicine. Jun. 2009;5(2):128-135.

Gad et al., Evaluation of the Toxicity of Intravenous Delivery of Auroshell Particles (Gold-Silica Nanoshells). Int J Toxicol. Nov.-Dec. 2012; 31(6):584-594.

Glazer et al., Biodistribution and acute toxicity of naked gold nanoparticles in a rabbit hepatic tumor model. Nanotoxicology. Dec. 2011;5(4):459-468.

Goodman et al., Toxicity of Gold Nanoparticles Functionalized with Cationic and Anionic Side Chains. Bioconjug Chem. Jul.-Aug. 2004;15(4):897-900.

Hainfeld et al., Gold nanoparticles: a new X-ray contrast agent. Br J Radiol. Mar. 2006;79(939):248-253.

Lasagna-Reeves et al., Bioaccumulation and toxicity of gold nanoparticles after repeated administration in mice. Biochem Biophys Res Commun. Mar. 19, 2010;393(4):649-655.

McBean and Katz, Laser Lipolysis: An Update. J Clin Aesthet Dermatol. Jul. 2011;4(7):25-34.

Mordon and Plot, Laser lipolysis versus traditional liposuction for fat removal. Expert Rev Med Devices. Nov. 2009;6(6):677-688.

Rastinehad et al., Gold nanoshell-localized photothermal ablation of prostate tumors in a clinical pilot device study. Proc Natl Acad Sci U S A. Sep. 10, 2019;116(37):18590-18596.

Rayavarapu et al., In vitro toxicity studies of polymer-coated gold nanorods. Nanotechnology. Apr. 9, 2010;21(14):145101.

Richardson et al., Experimental and theoretical studies of light-to-heat conversion and collective heating effects in metal nanoparticle solutions. Nano Lett. Mar. 2009;9(3):1139-1146.

Sandhu et al., Gold Nanoparticle-Mediated Transfection of Mammalian Cells. Bioconjug Chem. Jan.-Feb. 2002;13(1):3-6.

Sheng et al., A Single-Blind Study Evaluating the Efficacy of Gold Nanoparticle Photothermal Assisted Liposuction in an Ex Vivo Human Tissue Model. Aesthet Surg J. Oct. 15, 2018;38(11):1213-1224.

Sheng et al., Gold Nanoparticle-assisted Selective Photothermolysis of Adipose Tissue (NanoLipo). Plast Reconstr Surg Glob Open. Jan. 8, 2015;2(12):e283.

Song et al., Successful Salvage Brachytherapy after Infusion of Gold AuroShell Nanoshells for Localized Prostate Cancer in a Human Patient. Adv Radiat Oncol. Feb. 26, 2023;8(4):101202.

Yang et al., Tuning Cellular Response to Nanoparticles via Surface Chemistry and Aggregation. Small. Apr. 24, 2014;10(8):1642-1651.

Yao et al., Applications and safety of gold nanoparticles as therapeutic devices in clinical trials. J Pharm Anal. Sep. 2023;13(9):960-967.

Zhang et al., Influence of anchoring ligands and particle size on the colloidal stability and in vivo biodistribution of polyethylene glycol-coated gold nanoparticles in tumor-xenografted mice. Biomaterials. Apr. 2009;30(10):1928-1936.

Zhang et al., Nanoparticles in Medicine: Therapeutic Applications and Developments. Clin Pharmacol Ther. May 2008;83(5):761-769.

Zhang et al., Size-dependent in vivo toxicity of PEG-coated gold nanoparticles. Int J Nanomedicine. 2011;6:2071-2081.

Zhang et al., Toxicologic effects of gold nanoparticles in vivo by different administration routes. Int J Nanomedicine. Oct. 5, 2010;5:771-781.

Huang et al., "Gold nanoparticles: Optical properties and implementations in cancer diagnosis and photothermal therapy", Journal of Advanced Research (2010) 1, 13-28 (16 pages).

International Search Report and Written Opinion issued on Jan. 7, 2026 in PCT/US2025/047659 (13 pages).

* cited by examiner

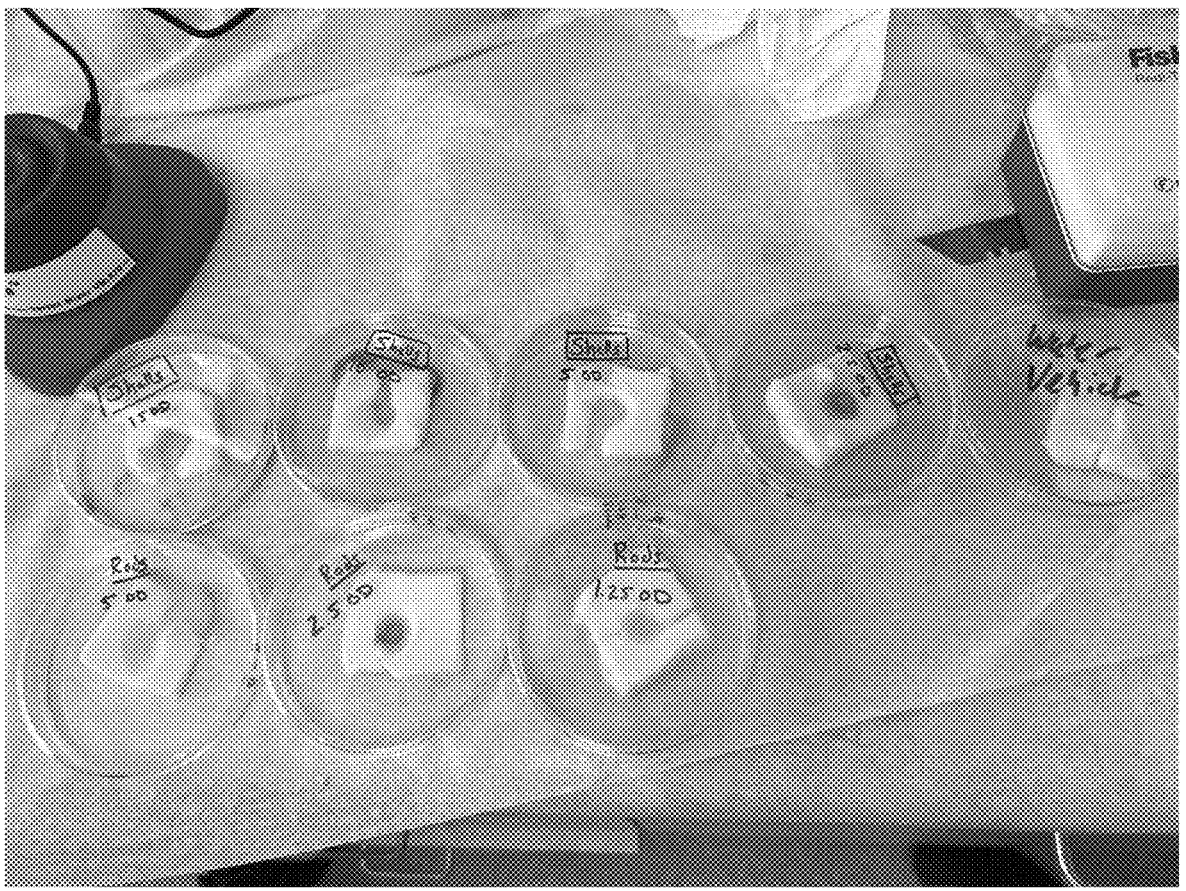
Figure 1: Butter pads after exposure to laser with either rods, shells, or vehicle (water) only.

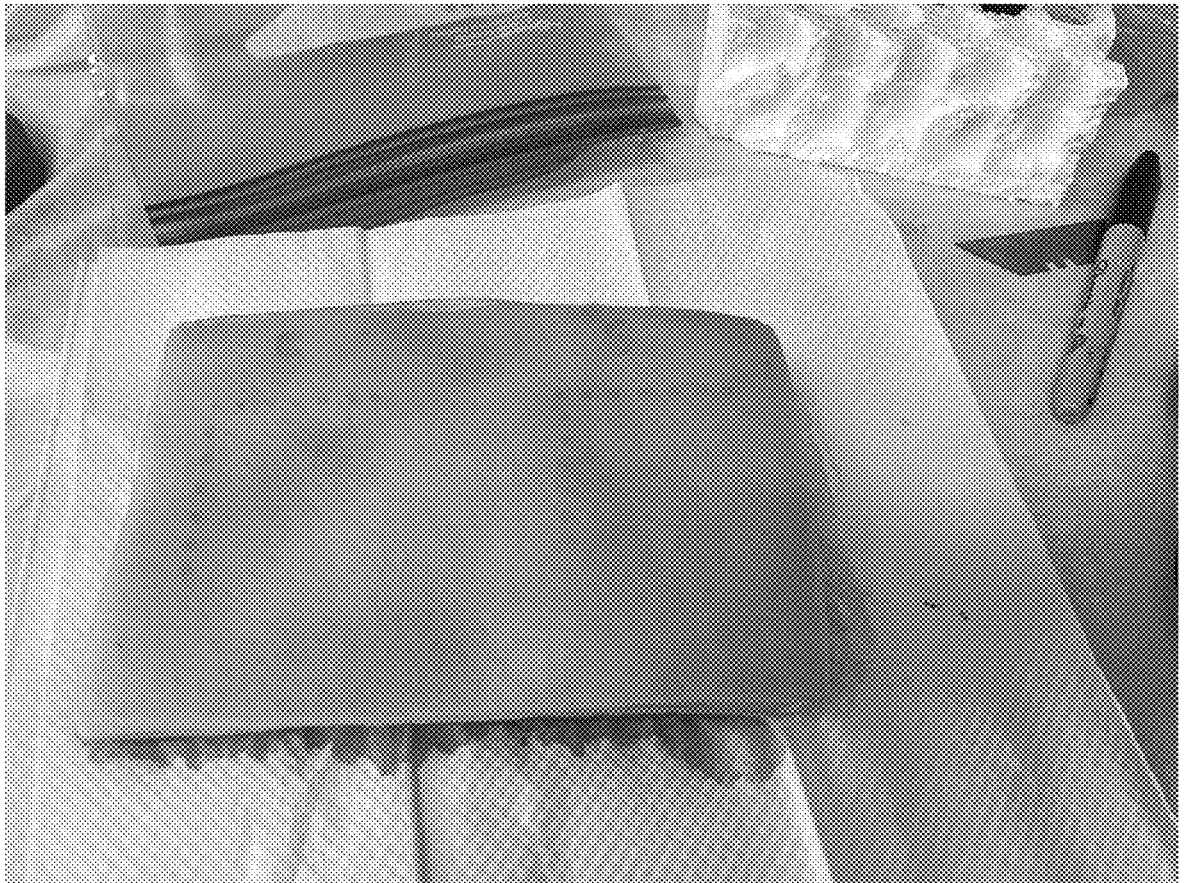
Figure 2: Porcine Tissue (Post treatment); solution can be observed in the treatment regions. Rods at 5 OD on the left, Shells at 10 OD on the right. Laser only was performed on the bottom middle region.

Figure 3: demonstration of the injection angle into the porcine tissue and device being injected as the needle is removed.

GOLD PARTICLES AND USES THEREOF

CROSS-REFERENCE TO RELATED APPLICATIONS

The present application claims the benefit of priority to U.S. Provisional Application No. 63/698,277 filed on Sep. 24, 2024, the contents of which are incorporated herein in their entirety.

FIELD

The present disclosure relates, at least in part, to uses of nanoparticles and in certain embodiments gold nanoshells.

BACKGROUND

U.S. Pat. No. 6,530,944 discloses "[a] method for inducing localized hyperthermia in a cell or tissue comprising the steps of delivering nanoparticles to said cell or tissue and exposing said nanoparticles to infrared radiation under conditions wherein said nanoparticles emit heat upon exposure to said infrared radiation."

PCT Patent Application No. WO2012/027728 (https://patents.google.com/patent/WO2012027728A2/en) discloses "nanoparticles and formulations which are useful for cosmetic, diagnostic and therapeutic applications to mammals such as humans." The nanoparticles of the '728 application can be "nanoplates, solid nanoshells, hollow nanoshells, nanorods, nanorice, nanospheres, nanofibers, nanowires, nanopyramids, nanoprisms, nanostars or a combination thereof" and that "[d]iseases or conditions suitable for treatment with subdermatological applications include wrinkles and tattoos. Other applications include skin rejuvenation and/or resurfacing, the removal or reduction of stretch marks and fat ablation."

PCT Patent Application No. WO2013/169955 (https://patents.google.com/patent/WO2013169955A1) discloses an "apparatus and method . . . [that] combines near infrared (NIR) light exposure and a solution of gold nanorods (GNRs) that may be injected into the treatment target in order to selectively heat fat in the target area."

PCT Patent Application No. WO2015054493 (https://patents.google.com/patent/WO2015054493A1) discloses "a material composition comprises a plurality of particles, wherein each particle comprises a core and a shell encapsulating the core, the shell comprising at least one atomic element not included in the core."

PCT Patent Application No. WO/2018/112261 (https://patents.google.com/patent/WO2018112261A1/) discloses "methods, systems, and devices for treating tissue ablation are disclosed" and that in "some embodiments, the system provides sub-ablative infrared radiation that is absorbed by nanoparticles."

SUMMARY

The present disclosure in various aspects and embodiments provides, inter alia, systems and methods for minimally-invasive lipolysis in a target area by injecting the area with a solution of photo-absorbing nanoparticles and irradiating the injected area with a beam of near infrared (NIR) light. The NIR emission wavelength may in certain embodiments be adapted to excite the nanoparticles to melt fat within the target area; in some embodiments so that the liquefied fat can be aspirated from the target area, or in some embodiments such that aspiration of the liquified fat is not needed. In certain aspects and embodiments the nanoparticles are be gold nanoshells; for example, spherical gold nanoshells.

As used herein the term "nanoparticle" means a particle having at least one axial dimension (diameter/length) that is between 1 and 1,000 nm. Nanoparticles suitable for use in conjunction with the present disclosure include any nanoparticle that is adapted to at least partially transduce an external energy into heat energy for elevating the temperature of a target area. Suitable examples of such nanoparticles and their methods of production and functionalization are known in the art. See e.g., U.S. Pat. Nos. 6,344,272 and 6,685,986; and PCT Patent Application Nos. WO2012/027728, WO2013/169955, WO2015054493, and WO/2018/112261—each of which are hereby incorporated by reference in their entirety herein. These transducing nanoparticles include, among others: nanoshells (including gold-shell silica core nanoshells, gold-gold sulfide nanoshells and other variants), metal nanorods, nanostars, hollow nanoparticles, nanocages, elliptical "nanorice," carbon particles, fullerenes, carbon fullerenes, metallic nanoparticles, metal colloids, carbon particles, carbon nanotubes, buckyballs, and any combination thereof. In some embodiments the nano particles are substantially spherical. In some embodiments the nano particles are spherical. In some embodiments, the nanoparticles have an aspect ratio in the range of 1:1 to 1:2. In some embodiments the nanoparticles comprise a core and a shell encapsulating the core, wherein said shell comprises at least one atomic element not included in the core. In some embodiments the nanoparticles have at least one axial dimension (diameter/length) longer than 100 nm.

As used herein, the term "nanoshell" means a nanoparticle that includes at least one non-conducting core layer and at least one conducting shell layer. In some embodiments the nanoshells are substantially spherical. In some embodiments the nanoshells are spherical. In some embodiments, the nanoshells have an aspect ratio in the range of 1:1 to 1:2. In some embodiments the nanoparticles have at least one axial dimension (diameter/length) longer than 100 nm.

In some embodiments, the non-conducting core of a nanoshell of the disclosure includes dielectric materials and/or semiconductors. In certain embodiments: the core includes one or more selected from the group consisting of silicon dioxide (silica), titanium dioxide, polymethyl methacrylate (PMMA), polystyrene, gold sulfide and macromolecules such as dendrimers. In some embodiments, the core includes one or more selected from the group consisting of CdSe, CdS or GaAs.

In some embodiments, the conducting shell layer of a nanoshell of the disclosure includes one or more metals selected from the group consisting of gold, silver, copper, platinum, palladium, lead, iron and the like. In some embodiments, the conducting shell layer includes gold. In some embodiments, the conducting shell layer includes silver.

Accordingly, in one aspect, a method for fat removal and/or skin tightening in a subject is provided wherein the method includes injecting a solution comprising a plurality of photo-absorbing nanoparticles into adipose tissue in a target area of said subject and delivering a series of pulses of near infrared light across an area of skin overlying the target area.

In another aspect, a method for fat removal and/or skin tightening in a subject is provided wherein the method includes injecting a solution comprising a plurality of photo-absorbing nanoparticles into adipose tissue in a target area of said subject and delivering a series of pulses of near infrared light across an area of skin overlying the target area; wherein said nanoparticles comprise at least one non-conducting core layer and at least one conducting shell layer.

In a further aspect, a method for fat removal and/or skin tightening in a subject is provided wherein the method includes injecting a solution comprising a plurality of photo-absorbing nanoparticles into adipose tissue in a target area of said subject and delivering a series of pulses of near infrared light across an area of skin overlying the target area; wherein said nanoparticles have at least one axial dimension (diameter/length) longer that 100 nm.

In yet another aspect, a method for fat removal and/or skin tightening in a subject is provided wherein the method includes injecting a solution comprising a plurality of photo-absorbing nanoparticles into adipose tissue in a target area of said subject and delivering a series of pulses of near infrared light across an area of skin overlying the target area; wherein said nanoparticles have an aspect ratio in the range of 1:1 to 1:2.

In an additional aspect, a method for fat removal and/or skin tightening in a subject is provided wherein the method includes injecting a solution comprising a plurality of photo-absorbing nanoparticles into adipose tissue in a target area of said subject and delivering a series of pulses of near infrared light across an area of skin overlying the target area; wherein said nanoparticles are substantially spherical.

In a further additional aspect, a method for fat removal and/or skin tightening in a subject is provided wherein the method includes injecting a solution comprising a plurality of photo-absorbing nanoparticles into adipose tissue in a target area of said subject and delivering a series of pulses of near infrared light across an area of skin overlying the target area; wherein said nanoparticles comprise a core and a shell encapsulating the core, wherein said shell comprises at least one atomic element not included in the core.

In some embodiments, a nanoshell of the disclosure has a diameter between 80-500 nm; or between 100-200 nm; or between 125-175 nm; or between 150-170 nm; or about 125 nm; or about 150 nm; or about 160 nm; or about 170 nm; or about 175 nm; or about 200 nm.

In some embodiments, a nanoshell of the disclosure has a diameter between 80-500 nm; or between 100-200 nm; or between 125-175 nm; or between 150-170 nm; or about 125 nm; or about 150 nm; or about 160 nm; or about 170 nm; or about 175 nm; or about 200 nm.

In some embodiments, a nanoshell of the disclosure has a conducting shell layer that is between 5 and 50 nm thick; or between 10 and 30 nm thick; or between 15 and 25 nm thick; or about 15 nm thick; or about 20 nm thick; or about 25 nm thick.

In some embodiments, a nanoshell of the disclosure has a conducting shell layer comprising gold that is between 5 and 50 nm thick; or between 10 and 30 nm thick; or between 15 and 25 nm thick; or about 15 nm thick; or about 20 nm thick; or about 25 nm thick.

In some embodiments, a nanoshell of the disclosure has a conducting shell layer comprising silver that is between 5 and 50 nm thick; or between 10 and 30 nm thick; or between 15 and 25 nm thick; or about 15 nm thick; or about 20 nm thick; or about 25 nm thick.

In some embodiments, nanoparticles of the disclosure comprise a core and a shell encapsulating the core, the shell comprising at least one atomic element not included in the core, wherein the cores have: a median maximum dimension that is less than 10 microns, and a median of at least one axial dimension that is in the range of 10 nm to 500 nm, and wherein the shells have: a median thickness that is less than 100 nm, a silicon concentration that is in the range of 10% to 50% on the basis of the weight of the shells, and an aluminum concentration that is in the range of 0.01% to 5% on the basis of the weight of the shells. In certain embodiments, nanoparticles of the disclosure comprise a core a core and a shell encapsulating the core, the shell comprising at least one atomic element not included in the core, wherein the cores have: a median maximum dimension that is less than 10 microns, and a median of at least one axial dimension that is in the range of 10 nm to 500 nm, and wherein the shells have: a median thickness that is less than 100 nm, a silicon concentration that is in the range of 10% to 50% on the basis of the weight of the shells, and an aluminum concentration that is in the range of 0.01% to 5% on the basis of the weight of the shells, wherein the shells have a ratio of the aluminum concentration to the silicon concentration in the range of 1:20 to 1:5000 such that the median thickness does not change by more than 10% when measured 24 hours after immersing in water. In certain embodiments, the nanoparticles are nanoshells (for example gold or silver nanoshells) in accordance with the claims of U.S. Pat. No. 9,9675,953.

In some embodiments of any of the methods described herein, the solution of photo-absorbing nanoparticles administered to the subject has nanoparticles in a concentration between 0.5 and 50 OD; or between 1 and 25 OD; or between 2.5 and 15 OD; or between 2 and 10 OD; or between 5 and 15 OD; or between 10 and 25 OD; or about 1 OD; or about 2 OD; or about 2.5 OD; or about 5 OD; or about 7 OD; or about 7.5 OD; or about 8 OD; or about 9 OD; or about 10 OD; or about 11 OD; or about 12 OD; or about 12.5 OD; or about 15 OD; or about 16 OD; or about 17 OD; or about 18 OD; or about 19 OD; or about 20 OD.

In some embodiments of any of the methods described herein, the solution of photo-absorbing nanoparticles administered to the subject has nanoparticles in a concentration less than 1.0 E 11 particles per mL; or less than 7.5 E 10 particles per mL; or less than 5 E10 particles per mL; or between 1.0 E 9 and 1.0 E 11 particles per mL; or between 2.0 E 9 and 5.0 E 10 particles per mL; or about 3.0 E 9 particles per mL; or about 3.5 E 9 particles per mL; or about 5.0 E 9 particles per mL; or about 7.0 E 9 particles per mL; or about 7.5 E 9 particles per mL; or about 1.0 E 10 particles per mL; or about 1.5 E 10 particles per mL; or about 2.0 E 10 particles per mL; or about 2.5 E 10 particles per mL; or about 5.0 E 10 particles per mL; or about 7.5 E 10 particles per mL.

In various embodiments of the methods described herein, the pulses of near infrared light are administered at 10-15 Joules per $cm^2$; or about 8 Joules per $cm^2$; or about 9 Joules per $cm^2$; or about 10 Joules per $cm^2$; or about 11 Joules per $cm^2$; or about 12 Joules per $cm^2$; or about 13 Joules per $cm^2$; or about 14 Joules per $cm^2$; or about 15 Joules per $cm^2$.

In some embodiments of the methods described herein, the pulses of near infrared light are administered at a wavelength between 750 nm to 1100 nm; or about 750 nm; or about 800 nm; or about 810 nm; or about 1064 nm.

In some embodiments, the pulses of near infrared light are administered at a frequency of 1-1000 Hz; 1-10 Hz, 10-100 Hz, 100-1000 Hz; or about 1 Hz; or about 2 Hz; or about 3 Hz; or about 4 Hz; or about 5 Hz; or about 6 Hz; or about 7 Hz; or about 8 Hz; or about 9 Hz; or about 10 Hz; or about 20 Hz; or about 25 Hz; or about 50 Hz; or about 100 Hz.

In some aspects and embodiments of the disclosure, a system is provided for fat removal and/or skin tightening in accordance with any of the methods provided herein, wherein the system comprises a solution of photo-absorbing nanoparticles as provided herein; a means for injecting the solution into the target area; and a near infrared light source for delivering a beam of light to the target area. In one embodiment the system further includes a means for extracting melted fat from the target area.

The terms "subject", "individual" or "patient" as used herein may be used interchangeably refer to a vertebrate, preferably a mammal. In some embodiments a subject or patient according to the disclosure is a human.

Further scope, applicability and advantages will become apparent from the non-restrictive detailed description given hereinafter. It should be understood, however, that this detailed description, while indicating exemplary embodiments or aspects, is given by way of example only.

BRIEF DESCRIPTION OF THE DRAWINGS

FIG. 1 shows butter pads after exposure to laser with either rods, shells, or vehicle (water) only.

FIG. 2 shows porcine tissue after treatment. Treatment with rods at 5 OD is on the left, and shells at 10 OD is on the right. Laser only was performed on the bottom middle region.

FIG. 3 shows the injection angle into the porcine tissue.

DETAILED DESCRIPTION

Nanoparticles

In certain embodiments of the disclosure the nanoparticles of the methods and compositions described herein are nanoshells. Nanoshell nanoparticles used in some embodiments of this disclosure may include a metallic shell and a non conducting, or dielectric core. These particles can be designed and constructed to absorb or scatter light at desired wavelengths. This "tunability" can be achieved by altering the ratio of the thickness of the metal shell to the non-conducting core.

The non-conducting core can be silica, but can be comprised of any dielectric material. Suitable dielectric materials include but are not limited to silicon dioxide, titanium dioxide, polymethyl methacrylate (PMMA), polystyrene, gold sulfide and macromolecules such as dendrimers. In some embodiments, core materials may be made of CdSe, CdS or GaAs.

In various embodiment the nonconducting core is surrounded by a layer that is made of a conducting material. Generally, the conducting layer is metallic but it may also be an organic conducting material such as polyacetylene, doped polyanaline and the like. Suitable metals include the noble and coinage metals but any metal that can conduct electricity is suitable. Metals that are particularly well suited for use in shells include but are not limited to gold, silver, copper, platinum, palladium, lead, iron or the like. Gold and silver are preferred in some embodiments. Alloys or non-homogenous mixtures of such metals may also be used. In some embodiments, the exterior shell of the nanoshell can be comprised of gold.

For many of the embodiments of this disclosure, nanoshell particles may be designed to absorb infrared light at wavelengths where light is not significantly absorbed by human tissue. Human tissue is minimally absorptive in the ranges from 750 nm to 1100 nm, often referred to as the "water window" or "tissue optical window". While solid gold nanoparticles and microparticles absorb light at wavelengths also absorbed by tissue, gold-coated nanoshell particles can be designed to absorb or scatter light within this "tissue optical window", enabling new in vivo applications. More specifically, the nanoshell particles used in the compositions and methods of the disclosure may include a thin gold shell, 10 to 30 nm thick, deposited on a solid silica (silicon dioxide) core.

Nanoparticles (such as nanoshells; eg gold nanoshells) of the disclosure can be added to polymers during their preparation by methods well known in the art. Suitable polymers include polyethylene, polyvinyl alcohol (PVA), latex, nylon, teflon, acrylic, kevlar, epoxy, glasses and the like. Solubility of nanoparticles into polymers can be facilitated by functionalization of the nanoparticle surfaces with suitable molecules known to those of skill in the art. To prevent aggregation of the particles in a saline environment and to provide steric hindrance in vivo, a 5,000 molecular weight (MW) methoxy-polyethylene glycol (PEG) chain can be attached through a thiol (sulphur) bond. The PEG coating in certain embodiments improves the stability of the nanoshell particles in an isotonic aqueous solution, and may also improve circulating half-life on administration.

Lasers and radiofrequency ablation devices may be used to thermally destroy tissue (such as adipose tissue) by delivery of energy at a rate in excess of the tissue's ability to dissipate the energy through blood perfusion thermal diffusion. In addition, some lasers provide energy at wavelengths naturally absorbed by chromaphores within tissue or blood, using the properties of tissue or blood as a natural absorber to convert the light to thermal energy. The result is either thermal coagulation of cells or tissue thermal fixation and the disruption of the vasculature. In many aspects and embodiments, nanoparticles (such as nanoshells) are designed to absorb near-infrared energy, transducing it into heat via surface plasmon resonance.

In various embodiments, the nanoparticles of the disclosure are nanoshells (for example gold or silver nanoshells). In certain embodiments embodiments, the nanoparticles of the disclosure are nanoshells (for example gold or silver nanoshells) such as described in, and or made by methods described in, for example, one or more of U.S. Pat. Nos. 6,344,272 and 6,685,986; and PCT Patent Application Nos. WO2012/027728, WO2013/169955, WO2015054493, and WO/2018/112261.

Certain nanoparticles, such as, for example, gold nanorods require use of cetyltrimethylammonium bromide (CTAB) to manufacture. There are concerns about the toxicity of CTAB (see for example the Santa Cruz Biotechnology Inc., MSDS for CTAB at https://datasheets.scbt.com/sc-278833.pdf). Thus, there may be risk that the use of CTAB could cause issues with the FDA and/or increased costs and efforts to remove CTAB and demonstrate the removal from each batch used. Moreover, CTAB is expensive and could result in an increase in the final cost of nanoparticles that require CTAB for manufacturing. Certain nanoshells (such as, e.g., certain gold nanoshells) as described herein can be manufactured without the use of CTAB. As such, in some embodiments, it may be useful to use nanoparticles that do not require CTAB for manufacturing.

Delivery of Near Infrared Light

In various embodiments, the target area where the nanoparticles were administered is exposed to pulses of near infrared light; for example using a laser. In various embodiments, the laser may be any one of many commercially available that are used for various dermatological and/or cosmetic purposes. One exemplary laser is the Palomar Vectus Laser. In some embodiments, the laser may be custom designed for a method of the disclosure. In certain embodiments, the target area is irradiated at a fluence of 1-60 Joules per $cm^2$; or 1-20 Joules per $cm^2$; or 5-15 Joules per $cm^2$; or 10-15 Joules per $cm^2$; or about 8 Joules per $cm^2$; or about 9 Joules per $cm^2$; or about 10 Joules per $cm^2$; or about 11 Joules per $cm^2$; or about 12 Joules per $cm^2$; or about 13 Joules per $cm^2$; or about 14 Joules per $cm^2$; or about 15 Joules per $cm^2$. In some embodiments, the near infrared light is administered with the laser wavelength between 750 nm to 1100 nm. In some embodiments the near infrared light is administered with the laser wavelength of about, e.g., 750 nm, 800 nm, 810 nm, or 1064 nm. Various repetition rates are may be used in different embodiments from continuous to pulsed, e.g., at 1-1000 Hz; 1-10 Hz, 10-100 Hz, 100-1000 Hz; or about 1 Hz; or about 2 Hz; or about 3 Hz; or about 4 Hz; or about 5 Hz; or about 6 Hz; or about 7 Hz; or about 8 Hz; or about 9 Hz; or about 10 Hz; or about 20 Hz; or about 25 Hz; or about 50 Hz; or about 100 Hz. While some energy is reflected, it is an advantage of the subject matter described herein is that a substantial amount of energy is absorbed by particles, with a lesser amount absorbed by skin.

To enable tunable destruction of target tissues, light-absorbing nanoparticles may be utilized in conjunction with a laser or other excitation source of the appropriate wavelength. The laser light may be applied continuously or in pulses with a single or multiple pulses of light. The intensity of heating and distance over which photothermal damage will occur are controlled by the intensity and duration of light exposure. In some embodiments, pulsed lasers are utilized in order to provide localized thermal destruction. In some such embodiments, pulses of varying durations are provided to localize thermal damage regions to within 0.05, 0.1, 0.5, 1, 2, 5, 10, 20, 30, 50, 75, 100, 200, 300, 500, 1000 microns of the particles. Pulses may in some embodiments be femtoseconds, picoseconds, microseconds, or milliseconds in duration. In some embodiments, the peak temperature realized in tissue from nanoparticle heating is at least 5, 10, 15, 20, 25, 30, 40, 50, 60, 70, 80, 90, 100, 200, 300, or 500 degrees Celsius.

Adipose Tissue Ablation

Liposuction evolved from work in the late 1960s from surgeons in Europe using primitive curettage techniques which were largely ignored, as they achieved irregular results with significant morbidity and bleeding. Modern liposuction first burst on the scene in a presentation by the French surgeon, Dr Yves-Gerard Illouz, in 1982. The "Illouz Method" featured a technique of suction-assisted lipolysis after tumesing or infusing fluid into tissues using blunt cannulas and high-vacuum suction and demonstrated both reproducible good results and low morbidity. During the 1980s, many United States surgeons experimented with liposuction, developing variations, and achieving mixed results. Most commonly, liposuction is performed on the abdomen and thighs in women, and the abdomen and flanks in men. According to the American Society for Aesthetic Plastic Surgery, liposuction was the most common plastic surgery procedure performed in 2006 with 403,684 patients.

Traditional liposuction relies on two techniques. The first technique employs a sharp, relatively large diameter (3 mm-5 mm) cannula that is manually manipulated to mechanically break fat down and while applying suction to remove the separated fat. A variation of this vacuum assisted technique is a mechanically powered cannula that reduces the surgeon's fatigue during large surface area liposuction procedures.

The second technique utilizes ultrasonic waves via a vibrating cannula, this technique is mechanical in its nature and significantly reduces the surgeon's fatigue factor. This technique induces the same or worse mechanical trauma to the tissues. Both techniques require significant amounts of fluid, known as a "tumescent solution," to be injected into the body to emulsify the fat, facilitating the removal of large volumes of fat while reducing blood loss and delivering a local anesthetic (lidocaine) to provide post-operative pain relief. While generally safe, lidocaine can be toxic, leading to serious complications, and even death.

A problem with the probes used in existing liposuction procedures is the generation of significant amounts of heat at the distal tip of the probe, which can exceed the temperature required for melting the fatty tissue. This excess heat can result in burning of tissue, damaging muscles or blood vessels, and even penetrating membranes such as the skin or the peritoneum that covers most of the intra-abdominal organs.

Alternative methods have been disclosed which exploit laser energy to remove unwanted fat. U.S. Pat. Nos. 6,605, 080 and 7,060,061 issued to Altshuler, et al. represent an alternative approach in which laser energy is externally applied to the skin to heat and melt fat tissues in epidermis and subcutaneous layers below. These patents disclose the use of near infrared radiation to heat-liquefy fat cells, after which the lipid pool is removed from the subcutaneous area by aspiration. Because of the considerable heat generation that results from the techniques, e.g., up to 70° C., at or in the fat tissue, a special cooling mechanism must be in place to prevent potential temporary skin damage or permanent scarring, with permanent scarring occurring primarily in the dermis. These methods present other limitations and potential adverse thermal effects on tissue above the lipid-rich tissue under treatment, including blistering, peeling, and depigmentation.

U.S. Pat. No. 8,430,919 of Bornstein discloses a lipolysis method in which the skin over the target site is optically irradiated with two different wavelengths of light, one in the near infrared (MR) region, the other in the infrared range, to modulate biochemical processes of adipocytes in the target site. In order to achieve the desired degree of fat removal, the duration of the treatment must be fairly long, from one to two hours, during which the patient must remain virtually motionless. Unless a sedative or general anesthesia has been administered to calm the patient, physical and psychological discomfort can ensue. NIR (700-950 nm) is preferable to other types of light for therapeutic use in biological systems because NIR light can pass through blood and tissue to depths of several inches. However, very few organic chromophores absorb in this region, and even fewer are capable of converting the absorbed energy into a chemical or thermal response that can be used to trigger drug release. A few years ago, gold nanostructures (shells, particles, rods, and cages) emerged as useful agents for photothermal therapy after they were shown to have strong absorption in the NIR region (four to five times higher than conventional photo-absorbing dyes) as well as tunable optical resonances. The strong absorption enables effective laser therapy at relatively low laser energies, rendering such therapy methods minimally invasive.

The present disclosure provides new methods (for example using gold nanoshells) for fat ablation and skin tightening that in certain embodiments may have advantages over previously used methods, such as advantages in safety and expense.

Administration

As used herein, the term "administer" an agent as described herein can include any route of introducing or delivering. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Systemic administration" refers to the introducing or delivering to a subject an agent via a route which introduces or delivers the agent to extensive areas of the subject's body (e.g., greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

In various aspects and embodiments the nanoparticles (eg., gold nanoshells) are administered by injection. In certain embodiments the nanoparticles (eg., gold nanoshells) are administered by injection into target areas having adipose tissue. In some the nanoparticles (eg., gold nanoshells) are administered by subcutaneous injection.

"Pharmaceutically acceptable carrier" (sometimes referred to as a "carrier") refers to a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

The term "modulate," "modulates," or "modulation" as used herein refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold and/or can be expressed in the enhancement and/or increase of a specified level and/or activity of at least about 1%, 5%, 10%, 15%, 25%, 35%, 40%, 50%, 60%, 75%, 80%, 90%, 95% or more.

The use of the terms "a" and "an" and "the" are to be construed to cover both the singular and the plural, unless otherwise indicated herein or clearly contradicted by context.

Unless specifically stated or obvious from context, as used herein the term "or" is understood to be inclusive and covers both "or" and "and".

The term "and/or" where used herein is to be taken as specific disclosure of each of the specified features or components with or without the other.

The terms "comprising", "having", "including", and "containing" are to be construed as open-ended terms (i.e., meaning "including but not limited to") unless otherwise noted. The term "consisting of" is to be construed as close-ended.

The term "about" or "approximately" shall generally mean within 20 percent, within 10 percent, or within 5, 4, 3, 2 or 1 percent of a given value or range. For the avoidance of doubt, the term about or approximately, when used in reference to a particular value contemplates and includes the particular specified value itself, for example the term "about 20" would specifically contemplate and include the value of exactly 20.

As used herein, the term "dosage period" refers to the period of time between dosage administration of a drug to a subject.

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Inhibit" or "reduce" or grammatical variations thereof as used herein refers to a decrease or diminishment in the specified level or activity of at least about 1, 5, 10, 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

"Treat," "treating" and similar terms as used herein in the context of treating a subject refer to providing medical and/or surgical management of a subject. Treatment may include, but is not limited to, administering an agent or composition (e.g., a pharmaceutical composition) to a subject. Treatment is typically undertaken in an effort to alter the course of a disease (which term is used to indicate any disease, disorder, syndrome, or undesirable condition warranting or potentially warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show evidence of a disease in order, e.g., to reduce the likelihood that the disease will occur, delay the onset of the disease, or to reduce the severity of the disease should it occur. The subject may have been identified as being at risk of developing the disease (e.g., at increased risk relative to the general population or as having a risk factor that increases the likelihood of developing the disease.

Selected Specific Embodiments

In addition to the aspects and embodiments disclosed elsewhere herein, the following particular embodiments are specifically contemplated.

1. A method for fat removal and/or skin tightening in a subject, said method comprising injecting a solution comprising a plurality of photo-absorbing nanoparticles into adipose tissue in a target area of said subject and delivering a series of pulses of near infrared light across an area of skin overlying the target area.

2. A method for fat removal and/or skin tightening in a subject, said method comprising injecting a solution comprising a plurality of photo-absorbing nanoparticles into adipose tissue in a target area of said subject and delivering a series of pulses of near infrared light across an area of skin overlying the target area; wherein said nanoparticles comprise at least one non-conducting core layer and at least one conducting shell layer.

3. A method for fat removal and/or skin tightening in a subject, said method comprising injecting a solution comprising a plurality of photo-absorbing nanoparticles into adipose tissue in a target area of said subject and delivering a series of pulses of near infrared light across an area of skin overlying the target area; wherein said nanoparticles have at least one axial dimension (diameter/length) longer that 100 nm.

4. A method for fat removal and/or skin tightening in a subject, said method comprising injecting a solution comprising a plurality of photo-absorbing nanoparticles into adipose tissue in a target area of said subject and delivering a series of pulses of near infrared light across an area of skin overlying the target area; wherein said nanoparticles have an aspect ratio in the range of 1:1 to 1:2.

5. A method for fat removal and/or skin tightening in a subject, said method comprising injecting a solution comprising a plurality of photo-absorbing nanoparticles into adipose tissue in a target area of said subject and delivering a series of pulses of near infrared light across an area of skin overlying the target area; wherein said nanoparticles are substantially spherical.

6. A method for fat removal and/or skin tightening in a subject, said method comprising injecting a solution comprising a plurality of photo-absorbing nanoparticles into adipose tissue in a target area of said subject and delivering a series of pulses of near infrared light across an area of skin overlying the target area; wherein said nanoparticles comprise a core and a shell encapsulating the core, wherein said shell comprises at least one atomic element not included in the core.

7. The method of any one of the previous embodiments, wherein the nanoparticles are nanoshells.

8. The method of any one of the previous embodiments, wherein the nanoparticles are nanoshells having a non-conducting core that comprises dielectric materials and/or semiconductor materials.

9. The method of any one of the previous embodiments, wherein the nanoparticles are nanoshells having a non-conducting core that comprises one or more dielectric materials selected from the group consisting of silicon dioxide (silica), titanium dioxide, polymethyl methacrylate (PMMA), polystyrene, gold sulfide and macromolecules such as dendrimers.

10. The method of any one of the previous embodiments, wherein the nanoparticles are nanoshells having a non-conducting core that comprises silicon dioxide (silica).

11. The method of any one of the previous embodiments, wherein the nanoparticles are nanoshells having a conducting shell layer comprising one or more metals selected from the group consisting of gold, silver, copper, platinum, palladium, lead, and iron.

12. The method of any one of the previous embodiments, wherein the nanoparticles are nanoshells having a conducting shell layer comprising one or more metals selected from the group consisting of gold and silver.

13. The method of any one of the previous embodiments, wherein the nanoparticles are nanoshells having a conducting shell layer comprising gold.

14. The method of any one of the previous embodiments, wherein the nanoparticles are nanoshells having a conducting shell layer comprising silver.

15. The method of any one of the previous embodiments, wherein the nanoparticles are nanoshells having a non-conducting core that comprises one or more dielectric materials selected from the group consisting of silicon dioxide (silica), titanium dioxide, polymethyl methacrylate (PMMA), polystyrene, gold sulfide and macromolecules such as dendrimers; and having a conducting shell layer having 16. The method of any one of the previous embodiments, wherein the nanoparticles are nanoshells having a non-conducting core that comprises one or more dielectric materials selected from the group consisting of silicon dioxide (silica), titanium dioxide, polymethyl methacrylate (PMMA), polystyrene, gold sulfide and macromolecules such as dendrimers; and having a conducting shell layer comprising one or more metals selected from the group consisting of gold, silver, copper, platinum, palladium, lead, and iron.

17. The method of any one of the previous embodiments, wherein the nanoparticles are nanoshells having a non-conducting core that comprises silicon dioxide (silica) and having a conducting shell layer comprising one or more metals selected from the group consisting of gold and silver.

18. The method of any one of the previous embodiments, wherein the nanoparticles are nanoshells having a non-conducting core that comprises silicon dioxide (silica) and having a conducting shell layer comprising gold.

19. The method of any one of the previous embodiments, wherein the nanoparticles are nanoshells having a non-conducting core that comprises silicon dioxide (silica) and having a conducting shell layer comprising silver.

20. The method of any one of the previous embodiments, wherein the nanoparticles are nanoshells having a diameter between 80-500 nm.

21. The method of any one of the previous embodiments, wherein the nanoparticles are nanoshells having a diameter between 100-200 nm.

22. The method of any one of the previous embodiments, wherein the nanoparticles are nanoshells having a diameter between 125-175 nm.
23. The method of any one of the previous embodiments, wherein the nanoparticles are nanoshells having a diameter between 150-170 nm.
24. The method of any one of the previous embodiments, wherein the nanoparticles are nanoshells having a diameter between 80-500 nm; or between 100-200 nm; or between 125-175 nm; or between 150-170 nm; or about 125 nm; or about 150 nm; or about 160 nm; or about 170 nm; or about 175 nm; or about 200 nm.
25. The method of any one of the previous embodiments, wherein the nanoparticles are nanoshells having a diameter of about 125 nm.
26. The method of any one of the previous embodiments, wherein the nanoparticles are nanoshells having a diameter of about 150 nm.
27. The method of any one of the previous embodiments, wherein the nanoparticles are nanoshells having a diameter of about 160 nm.
28. The method of any one of the previous embodiments, wherein the nanoparticles are nanoshells having a diameter of about 170 nm.
29. The method of any one of the previous embodiments, wherein the nanoparticles are nanoshells having a diameter of about 175 nm.
30. The method of any one of the previous embodiments, wherein the nanoparticles are nanoshells having a diameter of about 200 nm.
31. The method of any one of the previous embodiments, wherein the nanoparticles are nanoshells having a conducting shell layer that is between 5 and 50 nm thick; or between 10 and 30 nm thick; or between 15 and 25 nm thick; or about 15 nm thick; or about 20 nm thick; or about 25 nm thick.
32. The method of any one of the previous embodiments, wherein the nanoparticles are nanoshells having a conducting shell layer comprising gold that is between 5 and 50 nm thick; or between 10 and 30 nm thick; or between 15 and 25 nm thick; or about 15 nm thick; or about 20 nm thick; or about 25 nm thick.
33. The method of any one of the previous embodiments, wherein the nanoparticles are nanoshells having a conducting shell layer comprising silver that is between 5 and 50 nm thick; or between 10 and 30 nm thick; or between 15 and 25 nm thick; or about 15 nm thick; or about 20 nm thick; or about 25 nm thick.
34. The method of any one of the previous embodiments, wherein said solution comprises said nanoparticles at a concentration between 0.5 and 50 OD.
35. The method of any one of the previous embodiments, wherein said solution comprises said nanoparticles at a concentration between 1 and 25 OD.
36. The method of any one of the previous embodiments, wherein said solution comprises said nanoparticles at a concentration between 2.5 and 15 OD.
37. The method of any one of the previous embodiments, wherein said solution comprises said nanoparticles at a concentration between 2 and 10 OD.
38. The method of any one of the previous embodiments, wherein said solution comprises said nanoparticles at a concentration between 5 and 15 OD.
39. The method of any one of the previous embodiments, wherein said solution comprises said nanoparticles at a concentration between 10 and 25 OD.

40. The method of any one of the previous embodiments, wherein said solution comprises said nanoparticles at a concentration of about 1 OD.
41. The method of any one of the previous embodiments, wherein said solution comprises said nanoparticles at a concentration of about 2 OD.
42. The method of any one of the previous embodiments, wherein said solution comprises said nanoparticles at a concentration of about 2.5 OD.
43. The method of any one of the previous embodiments, wherein said solution comprises said nanoparticles at a concentration of about 5 OD.
44. The method of any one of the previous embodiments, wherein said solution comprises said nanoparticles at a concentration of about 7 OD.
45. The method of any one of the previous embodiments, wherein said solution comprises said nanoparticles at a concentration of about 7.5 OD.
46. The method of any one of the previous embodiments, wherein said solution comprises said nanoparticles at a concentration of about 8 OD.
47. The method of any one of the previous embodiments, wherein said solution comprises said nanoparticles at a concentration of about 9 OD.
48. The method of any one of the previous embodiments, wherein said solution comprises said nanoparticles at a concentration of about 10 OD.
49. The method of any one of the previous embodiments, wherein said solution comprises said nanoparticles at a concentration of about 11 OD.
50. The method of any one of the previous embodiments, wherein said solution comprises said nanoparticles at a concentration of about 12 OD.
51. The method of any one of the previous embodiments, wherein said solution comprises said nanoparticles at a concentration of about 12.5 OD.
52. The method of any one of the previous embodiments, wherein said solution comprises said nanoparticles at a concentration of about 13 OD.
53. The method of any one of the previous embodiments, wherein said solution comprises said nanoparticles at a concentration of about 14 OD.
54. The method of any one of the previous embodiments, wherein said solution comprises said nanoparticles at a concentration of about 15 OD.
55. The method of any one of the previous embodiments, wherein said solution comprises said nanoparticles at a concentration of about 16 OD.
56. The method of any one of the previous embodiments, wherein said solution comprises said nanoparticles at a concentration of about 17 OD.
57. The method of any one of the previous embodiments, wherein said solution comprises said nanoparticles at a concentration of about 18 OD.
58. The method of any one of the previous embodiments, wherein said solution comprises said nanoparticles at a concentration of about 19 OD.
59. The method of any one of the previous embodiments, wherein said solution comprises said nanoparticles at a concentration of about 20 OD.
60. The method of any one of the previous embodiments, wherein said solution comprises said nanoparticles at a concentration less than $1.0 \times 10^{11}$ particles per mL; or less than $7.5 \times 10^{10}$ particles per mL; or less than $5 \times 10^{10}$ particles per mL.
61. The method of any one of the previous embodiments, wherein said solution comprises said nanoparticles at a concentration between 1.0 E 9 and 1.0 E 11 particles per mL; or between 2.0 E 9 and 5.0 E 10 particles per mL.

62. The method of any one of the previous embodiments, wherein said solution comprises said nanoparticles at a concentration of about or about 3.0 E 9 particles per mL; or about 3.5 E 9 particles per mL; or about 5.0 E 9 particles per mL; or about 7.0 E 9 particles per mL; or about 7.5 E 9 particles per mL; or about 1.0 E 10 particles per mL; or about 1.5 E 10 particles per mL; or about 2.0 E 10 particles per mL; or about 2.5 E 10 particles per mL; or about 5.0 E 10 particles per mL; or about 7.5 E 10 particles per mL.

63. The method of any one of the previous embodiments, wherein said nanoparticles are nanoshells and said solution comprises said nanoshells at a concentration between 0.5 and 50 OD.

64. The method of any one of the previous embodiments, wherein said nanoparticles are nanoshells and said solution comprises said nanosheils at a concentration between 1 and 25 OD.

65. The method of any one of the previous embodiments, wherein said nanoparticles are nanoshells and said solution comprises said nanoshells at a concentration between 2.5 and 15 OD.

66. The method of any one of the previous embodiments, wherein said nanoparticles are nanoshells and said solution comprises said nanoshells at a concentration between 2 and 10 OD.

67. The method of any one of the previous embodiments, wherein said nanoparticles are nanoshells and said solution comprises said nanoshells at a concentration between 5 and 15 OD.

68. The method of any one of the previous embodiments, wherein said nanoparticles are nanoshells and said solution comprises said nanoshells at a concentration between 10 and 25 OD.

69. The method of any one of the previous embodiments, wherein said nanoparticles are nanoshells and said solution comprises said nanoshells at a concentration of about 1 OD.

70. The method of any one of the previous embodiments, wherein said nanoparticles are nanoshells and said solution comprises said nanoshells at a concentration of about 2 OD.

71. The method of any one of the previous embodiments, wherein said nanoparticles are nanoshells and said solution comprises said nanoshells at a concentration of about 2.5 OD.

72. The method of any one of the previous embodiments, wherein said nanoparticles are nanoshells and said solution comprises said nanoshells at a concentration of about 5 OD.

73. The method of any one of the previous embodiments, wherein said nanoparticles are nanoshells and said solution comprises said nanoshells at a concentration of about 7 OD.

74. The method of any one of the previous embodiments, wherein said nanoparticles are nanoshells and said solution comprises said nanoshells at a concentration of about 7.5 OD.

75. The method of any one of the previous embodiments, wherein said nanoparticles are nanoshells and said solution comprises said nanoshells at a concentration of about 8 OD.

76. The method of any one of the previous embodiments, wherein said nanoparticles are nanoshells and said solution comprises said nanoshells at a concentration of about 9 OD.

77. The method of any one of the previous embodiments, wherein said nanoparticles are nanoshells and said solution comprises said nanoshells at a concentration of about 10 OD.

78. The method of any one of the previous embodiments, wherein said nanoparticles are nanoshells and said solution comprises said nanoshells at a concentration of about 11 OD.

79. The method of any one of the previous embodiments, wherein said nanoparticles are nanoshells and said solution comprises said nanoshells at a concentration of about 12 OD.

80. The method of any one of the previous embodiments, wherein said nanoparticles are nanoshells and said solution comprises said nanoshells at a concentration of about 12.5 OD.

81. The method of any one of the previous embodiments, wherein said nanoparticles are nanoshells and said solution comprises said nanoshells at a concentration of about 13 OD.

82. The method of any one of the previous embodiments, wherein said nanoparticles are nanoshells and said solution comprises said nanoshells at a concentration of about 14 OD.

83. The method of any one of the previous embodiments, wherein said nanoparticles are nanoshells and said solution comprises said nanoshells at a concentration of about 15 OD.

84. The method of any one of the previous embodiments, wherein said nanoparticles are nanoshells and said solution comprises said nanoshells at a concentration of about 16 OD.

85. The method of any one of the previous embodiments, wherein said nanoparticles are nanoshells and said solution comprises said nanoshells at a concentration of about 17 OD.

86. The method of any one of the previous embodiments, wherein said nanoparticles are nanoshells and said solution comprises said nanoshells at a concentration of about 18 OD.

87. The method of any one of the previous embodiments, wherein said nanoparticles are nanoshells and said solution comprises said nanoshells at a concentration of about 19 OD.

88. The method of any one of the previous embodiments, wherein said nanoparticles are nanoshells and said solution comprises said nanoshells at a concentration of about 20 OD.

89. The method of any one of the previous embodiments, wherein said nanoparticles are nanoshells and said solution comprises said nanoshells at a concentration less than 1.0 E 11 particles per mL; or less than 7.5 E 10 particles per mL; or less than 5 E10 particles per mL.

90. The method of any one of the previous embodiments, wherein said nanoparticles are nanoshells and said solution comprises said nanoshells at a concentration between 1.0 E 9 and 1.0 E 11 particles per mL; or between 2.0 E 9 and 5.0 E 10 particles per mL.

91. The method of any one of the previous embodiments, wherein said nanoparticles are nanoshells and said solution comprises said nanoshells at a concentration of about or about 3.0 E 9 particles per mL; or about 3.5 E 9 particles per mL; or about 5.0 E 9 particles per mL;

or about 7.0 E 9 particles per mL; or about 7.5 E 9 particles per mL; or about 1.0 E 10 particles per mL; or about 1.5 E 10 particles per mL; or about 2.0 E 10 particles per mL; or about 2.5 E 10 particles per mL; or about 5.0 E 10 particles per mL; or about 7.5 E 10 particles per mL.

92. The method of any one of the previous embodiments, wherein said nanoparticles are manufactured without the use of CTAB.

93. The method of any one of the previous embodiments, wherein said nanoparticles are coated with PEG.

94. The method of any one of the previous embodiments, wherein said pulses of near infrared light are administered at 1-60 Joules per $cm^2$; or 1-20 Joules per $cm^2$; or 5-15 Joules per $cm^2$; or 5-10 Joules per $cm^2$, or 10-15 Joules per $cm^2$; or about 8 Joules per $cm^2$; or about 9 Joules per $cm^2$; or about 10 Joules per $cm^2$; or about 11 Joules per $cm^2$; or about 12 Joules per $cm^2$; or about 13 Joules per $cm^2$; or about 14 Joules per $cm^2$; or about 15 Joules per $cm^2$.

95. The method of any one of the previous embodiments, wherein said pulses of near infrared light are administered at 1-60 Joules per $cm^2$.

96. The method of any one of the previous embodiments, wherein said pulses of near infrared light are administered at 1-20 Joules per $cm^2$.

97. The method of any one of the previous embodiments, wherein said pulses of near infrared light are administered at 5-15 Joules per $cm^2$.

98. The method of any one of the previous embodiments, wherein said pulses of near infrared light are administered at 5-10 Joules per $cm^2$.

99. The method of any one of the previous embodiments, wherein said pulses of near infrared light are administered at 10-15 Joules per $cm^2$.

100. The method of any one of the previous embodiments, wherein said pulses of near infrared light are administered at about 1 Joules per $cm^2$; or about 2 Joules per $cm^2$; or about 3 Joules per $cm^2$; or about 4 Joules per $cm^2$; or about 5 Joules per $cm^2$ or about 6 Joules per $cm^2$; or about 7 Joules per $cm^2$; or about 8 Joules per $cm^2$; or about 9 Joules per $cm^2$; or about 10 Joules per $cm^2$; or about 11 Joules per $cm^2$; or about 12 Joules per $cm^2$; or about 13 Joules per $cm^2$; or about 14 Joules per $cm^2$; or about 15 Joules per $cm^2$.

101. The method of any one of the previous embodiments, wherein said pulses of near infrared light are administered at about 6 Joules per $cm^2$.

102. The method of any one of the previous embodiments, wherein said pulses of near infrared light are administered at about 12 Joules per $cm^2$.

103. The method of any one of the previous embodiments, wherein said pulses of near infrared light are administered at a wavelength between 750 nm to 1100 nm.

104. The method of any one of the previous embodiments, wherein said pulses of near infrared light are administered at a wavelength of about 750 nm.

105. The method of any one of the previous embodiments, wherein said pulses of near infrared light are administered at a wavelength of about 800 nm.

106. The method of any one of the previous embodiments, wherein said pulses of near infrared light are administered at a wavelength of about 810 nm.

107. The method of any one of the previous embodiments, wherein said pulses of near infrared light are administered at a wavelength of about 1064 nm.

108. The method of any one of the previous embodiments, wherein said pulses of near infrared light are administered at a frequency of 1-1000 Hz; 1-10 Hz, 10-100 Hz, 100-1000 Hz; or about 1 Hz; or about 2 Hz; or about 3 Hz; or about 4 Hz; or about 5 Hz; or about 6 Hz; or about 7 Hz; or about 8 Hz; or about 9 Hz; or about 10 Hz; or about 20 Hz; or about 25 Hz; or about 50 Hz; or about 100 Hz.

109. The method of any one of the previous embodiments, wherein said method further comprises aspirating a liquid from the target area, wherein the liquid comprises subcutaneous tissue and/or liquefied fat.

110. The method of any one of the previous embodiments, wherein said method does not comprise aspirating liquid having subcutaneous tissue and/or liquefied fat from the target area after said injecting nanoparticles and said delivering near infrared light.

111. A system for fat removal and/or skin tightening in accordance with any of the methods of the preceding embodiments, wherein the system comprises a solution of photo-absorbing nanoparticles as provided herein; a means for injecting the solution into the target area; and a near infrared light source for delivering a beam of light to the target area near infrared light source for delivering a beam of light to the target area.

112. A system for fat removal and/or skin tightening in accordance with any of the methods of the preceding embodiments, wherein the system comprises a solution of photo-absorbing nanoparticles as provided herein; a means for injecting the solution into the target area; a near infrared light source for delivering a beam of light to the target area near infrared light source for delivering a beam of light to the target area; and a means for extracting melted fat from the target area, The following examples are provided to further illustrate aspects and embodiments of the disclosure. These examples are non-limiting and should not be construed as limiting any aspects and embodiments of the disclosure.

EXAMPLES

Example 1: Comparison of Nanorods and Nanoshells

This experiment was designed to determine if 160 nm gold nanoshells could perform comparably to the 45 nm×15 nm gold nanorods in fat reduction technology. Both materials were developed to resonate at a similar wavelength of 800 nm. Properties of nanorods and nanoshells are shown on Table 1. The nanoshells were acquired from NanoComposix, Product Number: GSGH800 (Gold Nanoshells, Peak Absorbance @800 nm, PEG, NanoXact™). The nanoshells, but not the nanorods, used in these experiments were made without the use of CTAB. For these experiments, butter pads were sectioned and placed in petri dishes with a divot in the center of each pad to retain the devices full volume. The devices were distributed to their respectively labeled dishes, and exposed to the 800 nm laser for an equivalent number of pulses. Based off the melting results of the butter, operators selected nanorods at 5 OD and nanoshells at 10 OD to be tested in porcine belly tissue due to the substantial fat release observed, however fat release was observed at all concentrations tested in the butter. After injecting the two devices in marked areas of the tissue in a grid pattern, dispensing approximately equal volumes in each area, the areas were exposed to the 800 nm laser for an equivalent number of pulses. Overall, the new nanoshells were found to produce a similar, if not better effect in melting butter and comparable results with regard to porcine tissue softening.

Materials

Butter and Porcine Tissue (Pork Belly)

Gold Nanoshells (32.3 OD, 1.04 mgAu/mL, 4.5 E 10 particles/mL); stored in 4 C

Gold Nanorods (46.5 OD, 0.79 mgAu/mL, 7.8 E 12 particles/mL); stored in 4 C

Sterile Water (Vehicle)

15 mL Eppendorf tubes

P1000 and P200 Pipettes and tips 3 mL syringe with 23 g injection needle 800 nm Laser Palomar Vectus Laser with 8.7 cm$^2$ spot size was used for this test Vortex mixer

TABLE 1

Comparison of Exemplary Gold Nanorods and Gold Nanoshells.

| | Gold Nanorods | Gold Nanoshells |
|---|---|---|
| Size | 15 nm × 50 nm | 160 nm diameter (gold shell thickness 20 nm ± 7 nm) |
| Absorption | 800 nm | 800 nm |
| Pegylated | Yes, mPEG 5 kDa | Yes, mPEG 5 kDa |
| Absorption to total extinction ratio | 0.88 | 0.23 |
| OD for equivalent absorption | 50 | 190 |
| Mass Concentration Au (mgAu/mL) | 0.8 | 7.0 |
| Particle Concentration (#/mL) | 8E+12 | 3E+11 |
| pH | 5.5 ± 0.5 | 5.0-7.5 |
| Solvent | USP Water | USP Water |
| Zeta Potential (mV) | −50 mV to −1 mV | −45 mV to −15 mV |

Procedures

Butter Test:

Dilute the two different particles to the dilutions in Table 1 and 2 using sterile water.

Power on the laser.

Laser used was the Palomar Vectus Laser

Settings: Blonde (Hair color), High (Hair Density), Type I (Skin Type), Coarse (Hair diameter), 45 ms pulse at 12 J/cm$^2$ Prepare and label petri dishes with pads of butter, making a small divot in the center of the butter deep enough to hold at least 200 uL of test solution.

Dispense 200 uL of each test solution into the appropriately labeled divots in the butter.

Deliver 40 consecutive pulses to each sample and record results.

Porcine Tissue Test (Pig Belly):

Select one concentration that showed good melting results in the butter for injection into the porcine tissue.

Label a 2"×2" area with equally spaced injection sites to form a 7×7 grid.

Mark an area of treatment with just the laser.

Palpate the treatment regions to note the relative firmness before treatment.

Using an injection needle and syringe, insert the needle in the marked grid, holding the syringe at such an angle that the test solutions are injected into the fat layer of the tissue.

Depress the plunger slowly as the syringe is withdrawn to allow the space to fill with the test solutions, dispensing roughly 3 mL between all injections (some volume leaked out).

Repeat the previous two steps for the remaining marked injection sites.

Wipe off the skin to remove any amount of solution that may have leaked out to ensure a clean treatment area.

Deliver 40 consecutive pulses to the sample area and record the results.

Settings: Blonde (Hair color), High (Hair Density), Type I (Skin Type), Coarse (Hair diameter), 45 ms pulse at 12 J/cm$^2$

TABLE 2

| Nanorods | | |
|---|---|---|
| OD | mgAu/mL | Particles/mL |
| 1.25 | 0.021 | 2.098 E 11 |
| 2.5 | 0.043 | 4.20 E 11 |
| 5 | 0.085 | 8.39 E 11 |

TABLE 3

| Nanoshells | | |
|---|---|---|
| OD | mgAu/mL | Particles/mL |
| 2.5 | 0.08 | 3.48 E 9 |
| 5 | 0.16 | 6.98 E 9 |
| 10 | 0.32 | 1.40 E 10 |
| 15 | 0.48 | 2.09 E 10 |

Results

The nanoshells and nanorods were diluted using sterile water from their stock concentrations of 32.3 OD and 46.5 OD, respectively, to the final concentrations for testing (see Table 1 and 2). Butter pads were placed into individually labeled petri dishes and a small indentation was pressed into the center. Each dilution was vortexed thoroughly to mix before 200 uL of the test solutions were deposited on the respective butter pads, in the divots. The solution was dispensed slowly in order to ensure the full volume was retained in the divots. The laser was prepared at the following settings: Blonde (Hair color), High (Hair Density), Type I (Skin Type), Coarse (Hair diameter), 45 ms pulse at 12 J/cm$^2$. The butter with the various test solutions was exposed to 40 consecutive pulses while observed for melting. The laser head was held approximately ¾" from the sample and maintained in the same position during the laser treatment. The effective area of the laser was more than sufficient to cover the size of the treatment area. Melting was observed at all tested concentrations to varying degrees, with the vehicle only sample producing no visible melting (FIG. 1).

Based off the results of the butter melting, one concentration from each test device was selected for testing in the porcine tissue. The tissue was roughly 1" thick, with about a ¼" fat pad under the skin. The tissue was marked on the skin with a grid, and palpated to feel for firmness in the tissue. The operators elected to inject the rods at 5 OD, and the shells at 10 OD to ensure a robust response from both devices. Fourteen (14) injections were made in a 2"×2" region in a 7×7 grid on the porcine tissue (FIGS. 2 and 3), dispensing roughly 3 mL of device in each region between the injections, with the operators wiping the area clean after all injections were performed. The two areas, as well as an untreated area were exposed to 40 pulses of the laser at the same settings as the butter. The 3 treated areas were then palpated after treatment and observations about tissue temperature and firmness were made. Both regions treated with the nanoparticles presented noticeable changes in the firmness of the tissue, with the changes not observed outside of the area injected. No palpable change was noted in the laser only treated region. Overall, there appeared to be a similar result in the porcine tissue between the 5 OD nanorods and the 10 OD nanoshells in the change of local firmness in the treated regions.

In these studies, the nanoshell device provided similar, if not better, results for the release of fat as the previously used nanorods.

The aspects, embodiments and examples described herein are illustrative and are not meant to be limitative. Variations of the foregoing embodiments, including alternatives, modifications and equivalents, are intended by the inventors to be encompassed by the present disclosure. Citations (including any publication or patent document and the like) listed in the present application are incorporated herein by reference in their entirety to the same extent as if individually incorporated by reference.

What is claimed is:

1. A method for localized thermal ablation of adipose tissue in a subject, comprising:

locally administering a solution comprising a plurality of nanoshells that absorb light at near infrared (NIR) wavelengths by subcutaneous injection of the solution into one or more locations within a target adipose tissue of the subject, thereby delivering the nanoshells immediately adjacent to the point of administration within the target adipose tissue, wherein the solution comprises the plurality of nanoshells at a concentration between $1.0 \times 10^9$ and $1.0 \times 10^{11}$ particles per mL, wherein the nanoshells comprise an overall diameter of between 150-170 nm, a gold outer shell of between 15 and 25 nm thickness that converts absorbed NIR light into heat via surface plasmon resonance, and a silicon dielectric core, and wherein cetyltrimethylammonium bromide (CTAB) is not used in the manufacture of the nanoshells; and delivering NIR light across an area of skin overlying the target adipose tissue to induce surface plasmon resonance from the injected nanoshells, thereby causing localized thermal ablation within the target adipose tissue, wherein the localized thermal ablation is melting of fat within the target adipose tissue.

2. A method according to claim 1, wherein the nanoshells are spherical.

3. A method according to claim 1, wherein the nanoshells are stabilized by polyethylene glycol.

4. A method according to claim 3, wherein the NIR light is administered in a pulsed manner.

5. A method according to claim 4, wherein the solution comprises a pharmaceutically acceptable carrier.

6. A method according to claim 5, wherein the wavelength of the NIR light is between 750 nm and 1100 nm.

7. A method according to claim 1, wherein the nanoshells are stabilized by polyethylene glycol.

8. A method according to claim 1, wherein the NIR light is administered in a pulsed manner.

9. A method according to claim 1, wherein the solution comprises a pharmaceutically acceptable carrier.

10. A method according to claim 1, wherein the wavelength of the NIR light is between 750 nm and 1100 nm.

11. A method according to claim 1, further comprising extracting the melted fat from the target adipose tissue.

12. A method for localized thermal ablation of adipose tissue in a subject, comprising:

locally administering a solution comprising a plurality of nanoshells that absorb light at near infrared (NIR) wavelengths by subcutaneous injection of the solution into one or more locations within a target adipose tissue of the subject, thereby delivering the nanoshells immediately adjacent to the point of administration within the target adipose tissue, wherein the solution comprises the plurality of nanoshells at a concentration between $1.0 \times 10^9$ and $1.0 \times 10^{11}$ particles per mL, wherein the nanoshells comprise an overall diameter of between 150-170 nm, a gold outer shell of between 15 and 25 nm thickness that converts absorbed NIR light into heat via surface plasmon resonance, and a silicon dielectric core; and delivering NIR light across an area of skin overlying the target adipose tissue to induce surface plasmon resonance from the injected nanoshells, thereby causing localized thermal ablation within the target adipose tissue, wherein the localized thermal ablation is melting of fat within the target adipose tissue, wherein the method does not comprise aspirating liquid having subcutaneous tissue and/or liquefied fat from the target adipose tissue after the subcutaneous injection of the nanoshells and the delivery of NIR light.

13. A method according to claim 12, wherein the nanoshells are spherical.

14. A method according to claim 12, wherein the nanoshells are stabilized by polyethylene glycol.

15. A method according to claim 14, wherein the NIR light is administered in a pulsed manner.

16. A method according to claim 15, wherein the solution comprises a pharmaceutically acceptable carrier.

17. A method according to claim 16, wherein the wavelength of the NIR light is between 750 nm and 1100 nm.

* * * * *